(12) United States Patent
Parthasarathy et al.

(10) Patent No.: US 12,377,062 B2
(45) Date of Patent: Aug. 5, 2025

(54) ANTIMICROBIAL SOLUTIONS (71) Applicant: Solventum Intellectual Properties Company, Maplewood, MN (US)

(72) Inventors: Ranjani V. Parthasarathy, Woodbury, MN (US); Joshua E. Schumaker, Minneapolis, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 849 days.

(21) Appl. No.: 17/619,373

(22) PCT Filed: Jun. 18, 2020

(86) PCT No.: PCT/IB2020/055738
§ 371 (c)(1),
(2) Date: Dec. 15, 2021

(87) PCT Pub. No.: WO2020/255036
PCT Pub. Date: Dec. 24, 2020

(65) Prior Publication Data
US 2022/0347128 A1    Nov. 3, 2022

Related U.S. Application Data

(60) Provisional application No. 62/864,187, filed on Jun. 20, 2019.

(51) Int. Cl.
| | | |
|---|---|---|
| A61K 8/39 | (2006.01) |
| A01N 31/02 | (2006.01) |
| A01N 33/12 | (2006.01) |
| A01N 43/40 | (2006.01) |
| A01N 47/44 | (2006.01) |
| A61K 8/42 | (2006.01) |
| A61K 8/43 | (2006.01) |
| A61K 8/84 | (2006.01) |
| A61K 8/86 | (2006.01) |
| A61K 9/00 | (2006.01) |
| A61K 9/08 | (2006.01) |
| A61K 31/155 | (2006.01) |
| A61K 31/444 | (2006.01) |
| A61K 31/785 | (2006.01) |
| A61K 45/00 | (2006.01) |
| A61K 47/10 | (2017.01) |
| A61K 47/14 | (2017.01) |
| A61P 1/02 | (2006.01) |
| A61P 15/02 | (2006.01) |
| A61P 17/00 | (2006.01) |
| A61P 17/02 | (2006.01) |
| A61P 31/02 | (2006.01) |
| A61P 31/04 | (2006.01) |
| A61P 31/10 | (2006.01) |
| A61P 31/12 | (2006.01) |
| A61Q 5/00 | (2006.01) |
| A61Q 19/10 | (2006.01) |

(52) U.S. Cl.
CPC .......... A61K 31/155 (2013.01); A61K 9/0014 (2013.01); A61K 9/08 (2013.01); A61K 47/10 (2013.01); A61P 31/02 (2018.01)

(58) Field of Classification Search
CPC . A61K 8/345; A61K 8/39; A61K 8/42; A61K 8/43; A61K 8/4926; A61K 8/84; A61K 8/86; A61K 9/08; A61K 9/0014; A61K 31/155; A61K 31/444; A61K 31/785; A61K 45/00; A61K 47/10; A61K 47/14; A61K 47/18; A61K 2300/00; A61P 1/02; A61P 15/02; A61P 17/00; A61P 17/02; A61P 31/02; A61P 31/04; A61P 31/10; A61P 31/12; A01N 31/02; A01N 33/12; A01N 43/40; A01N 47/44; A61Q 5/00; A61Q 17/005; A61Q 19/10
See application file for complete search history.

(56) References Cited

U.S. PATENT DOCUMENTS

| 6,211,139 B1 | 4/2001 | Keys |
| 2009/0186943 A1 | 7/2009 | Ikeda |
| 2016/0074517 A1 | 3/2016 | Nguyen-Kim |

FOREIGN PATENT DOCUMENTS

| DE | 10016875 | 10/2001 |
| EP | 1955691 | 8/2008 |
| WO | WO 2001-014313 | 3/2001 |
| WO | WO 2011-023887 | 3/2011 |
| WO | WO 2016/019174 A1 | 2/2016 |

OTHER PUBLICATIONS

Griffin, "Calculation of HLB Values of Non-Ionic Surfactants", Journal of the Society of Cosmetic Chemists, Dec. 1954, vol. 5 No. 4, pp. 249-256.
Wenninger, "International Cosmetics Ingredient Dictionary and Handbook," 7th Edition, Published by The Cosmetic, Toiletry, and Fragrance Association, 1997, vol. 2, 4 pages.
International Search Report for PCT Application No. PCT/IB2020/055738, mailed on Nov. 23, 2020, 8 pages.

*Primary Examiner* — Brenda L Coleman (57) ABSTRACT

An antimicrobial composition includes an aqueous carrier and a surfactant system. The surfactant system includes a first surfactant including a first polyethylene glycol (PEG) compound with an HLB value of greater than about 10 and less than about 14, and a second surfactant different from the first surfactant, wherein the second surfactant has an HLB value less than about 10.

17 Claims, 1 Drawing Sheet

ANTIMICROBIAL SOLUTIONS

BACKGROUND

Routine pre-operative cleansing of the skin, mucosae, wound or surgical site with an antiseptic is important to prepare a patient for a surgical procedure. The purpose of preoperative skin antisepsis is to reduce the bioburden of microorganisms on the skin and thus reduce the risk of inoculation of the surgical site with potentially infecting organisms that reside on the skin.

Bacterial bioburden should be maintained as low as possible prior to making an incision, during surgery, and after closing the incision to reduce the rate of surgical site infections. Some common preoperative skin preparations include lower monohydric alcohols such as, for example, isopropyl alcohol (IPA), in combination with antiseptic compounds such as chlorhexidine, and iodine/iodophors. These preoperative skin preparations are fast-acting antiseptics (due to the alcohol) with persistent activity (due to the chlorhexidine or iodophor). These antiseptic compounds are effective against gram positive and gram negative bacteria, fungi and most viruses, and kill microbes by destroying the cell membrane. The antiseptic compounds also bind to the surface of the skin and can be released over time, which can provide persistent antimicrobial activity. For example, in the case of chlorhexidine, an antimicrobial count does not return to a base line within a six hour period.

There is a need to improve the persistence of antimicrobial bathing products, but good efficacy against a wide range of microbes can be important for many pre- and post-surgical applications. Recently, the U.S. Food and Drug Administration (FDA) provided criteria for surgical prep solutions, and in pertinent part these criteria require that the active antimicrobial ingredient in a solution should show a clear difference in efficacy at 10 minutes compared to the solution vehicle (the solution without the antimicrobial ingredient). In light of these FDA criteria, there is a need for an antimicrobial patient bathing solution that shows differentiation of the vehicle from the active antimicrobial ingredient at 10 minutes, but that also demonstrates good 24 hour efficacy against a wide variety of microorganisms.

SUMMARY

A hydrophilic antiseptic like chlorhexidine can penetrate the first few layers of the stratum corneum in the skin, but can go no deeper. However, bacteria are present in the deeper layers of the skin and can resurface to cause infections. To provide an effective combination of antimicrobial properties, it can be important for an antimicrobial solution to kill bacteria in the deeper layers of the stratum corneum, but also to ensure that sufficient antiseptic remain on the surface of a treatment area such as the skin, mucosa, body cavity, wound, or surgical site to provide excellent persistence.

Polyethylene glycol (PEG) compounds can reach the deeper layers of the stratum corneum, and can also act as solubilizers to improve transport of cationic antiseptics to deeper skin layers, both of which can improve antimicrobial persistence. In general, the present disclosure is directed to antimicrobial patient preps and patient bathing solutions that include one or more PEG compounds used alone or in combination with an optional antiseptic compound. The patient preps/bathing solutions including one or more PEG compounds access bacteria on the skin very effectively, and the surfactant properties of the PEG compounds can provide have good antimicrobial persistence over extended periods of time. When used in combination with a cationic antiseptic, the patient preps/bathing solutions including one or more PEG compounds can provide an even more effective combination of antimicrobial efficacy and persistence, and can satisfy FDA criteria requiring differentiation of the vehicle from the active antimicrobial ingredient at 10 minutes, while also having good 24 hour efficacy against a wide variety of microorganisms.

In other embodiments, the patient preps/bathing solutions can further optionally include alkyl esters, which may or may not include PEG. Patient preps/bathing solutions including alkyl esters provide excellent longer term antimicrobial efficacy when used with antiseptics, but solution vehicles including alkyl esters also can have good antimicrobial activity over shorter time periods, which can be useful in formulating solutions meeting various aspects of the applicable FDA criteria.

Patient preps can include not only topical surfaces like the skin and hair of a patient, but also mucosal surfaces like the mouth, vagina, and preps for any interior body cavity like a wound or a surgical site.

In one aspect, the present disclosure is directed to an antimicrobial composition, including: an aqueous carrier; and a surfactant system including: a first surfactant including a first polyethylene glycol (PEG) compound with an HLB value of greater than about 10 and less than about 14, and a second surfactant different from the first surfactant, wherein the second surfactant has an HLB value less than about 10.

In another aspect, the present disclosure is directed to an antimicrobial composition, including: an aqueous carrier; and a surfactant system including: a first surfactant including a polyethylene glycol (PEG) compound with an HLB value of greater than about 10 and less than about 18, and a second surfactant different from the first surfactant, wherein the second surfactant includes a PEG alkyl ester with an HLB value less than about 10, wherein the alkyl group of the PEG alkyl ester has 8 to 22 carbon atoms.

In another aspect, the present disclosure is directed to an antimicrobial composition, including: about 5 wt % to about 95 wt % of an aqueous carrier, based on the total weight of the composition; about 1 wt % to about 10 wt %, based on the total weight of the composition, of a first surfactant including a first polyethylene glycol (PEG) compound with an HLB value of greater than about 10 and less than about 14; and about 1 wt % to about 10 wt %, based on the total weight of the composition, of a second surfactant, different from the first surfactant, wherein the second surfactant has an HLB value of less than about 10, and wherein the second surfactant is chosen from an alkyl ester, an alkyl ether, an alkyl amide, and mixtures and combinations thereof, wherein the alky ester, alkyl ether, and alkyl amide have an alkyl group independently selected to have 8 to 22 carbon atoms.

In another aspect, the present disclosure is directed to a method of disinfecting a treatment site chosen from skin, hair, mucosae, wounds, and body cavities, the method including applying to the treatment site an antimicrobial composition. The antimicrobial composition includes: about 5 wt % to about 95 wt % of an aqueous carrier, based on the total weight of the composition; about 1 wt % to about 10 wt %, based on the total weight of the composition, of a first surfactant including a first polyethylene glycol (PEG) compound with an HLB value of greater than about 10 and less than about 14; about 1 wt % to about 10 wt %, based on the total weight of the composition, of a second surfactant, different from the first surfactant, wherein the second surfactant has an HLB value of less than about 10, and wherein the second surfactant is chosen from chosen from alkyl esters, alkyl ethers, alkyl amides, and mixtures and combinations thereof, wherein the alkyl esters, alkyl ethers, and alkyl amides have an alkyl group independently selected to have 8 to 22 carbon atoms; and about 1% to about 10% by weight, based on the total weight of the composition, of a cationic antiseptic chosen from octenidine, biguanides, bisbiguanides, polymeric biguanides, polymeric (bis) biguanides, benzalkonium chloride, alexidine dihydrochloride, cetyl pyridinium chloride, salts thereof and mixtures and combinations thereof.

In another aspect, the present disclosure is directed to a kit with an antimicrobial composition and an applicator for the antimicrobial composition. The antimicrobial composition includes: about 5 wt % to about 95 wt % of an aqueous carrier, based on the total weight of the composition; about 1 wt % to about 10 wt %, based on the total weight of the composition, of a first surfactant including a polyethylene glycol (PEG) compound with an HLB value of greater than about 10 and less than about 14; about 1 wt % to about 10 wt %, based on the total weight of the composition, of a second surfactant, different from the first surfactant, wherein the second surfactant has an HLB value of less than about 10, and wherein the second surfactant is chosen from chosen from alkyl esters, alkyl ethers, alkyl amides, and mixtures and combinations thereof, wherein the alkyl esters, alkyl ethers, and alkyl amides have an alkyl group independently selected to have 8 to 22 carbon atoms; and about 1% to about 10% by weight, based on the total weight of the composition, of a cationic antiseptic chosen from octenidine, biguanides, bisbiguanides, polymeric biguanides, polymeric (bis) biguanides, benzalkonium chloride, alexidine dihydrochloride, cetyl pyridinium chloride, salts thereof and mixtures and combinations thereof.

In another aspect, the present disclosure is directed to an antimicrobial composition including a vehicle and a cationic antiseptic. The vehicle includes an aqueous carrier and a surfactant system including a PEG compounds with an HLB value of greater than about 8 and less than about 14.

In another aspect, the present disclosure is directed to an antimicrobial composition, including: about 5 wt % to about 95 wt % of an aqueous carrier, based on the total weight of the composition; about 1 wt % to about 10 wt %, based on the total weight of the composition, of a first surfactant including a PEG compound with an HLB value of greater than about 8 and less than about 14; and about 1 wt % to about 10 wt %, based on the total weight of the composition, of a cationic antiseptic chosen from octenidine, biguanides, bisbiguanides, polymeric biguanides, polymeric (bis) biguanides, benzalkonium chloride, alexidine dihydrochloride, cetyl pyridinium chloride, and mixtures and combinations thereof.

In another aspect, the present disclosure is directed to a method of disinfecting mammalian skin including applying to the mammalian skin an antimicrobial composition. The antimicrobial composition includes: about 5 wt % to about 95 wt % of an aqueous carrier, based on the total weight of the composition; about 1 wt % to about 10 wt %, based on the total weight of the composition, of a first surfactant including a PEG compound with an HLB value of greater than about 8 and less than about 14; and about 1 wt % to about 10 wt %, based on the total weight of the composition, of a cationic antiseptic.

In another aspect, the present disclosure is directed to a kit including an antimicrobial composition and an applicator for applying the antimicrobial composition to a treatment site. The antimicrobial composition includes: about 5 wt % to about 95 wt % of an aqueous carrier, based on the total weight of the composition; about 1 wt % to about 10 wt %, based on the total weight of the composition, of a surfactant including a PEG compound with an HLB value of greater than about 8 and less than about 14; and about 1 wt % to about 10 wt %, based on the total weight of the composition, of a cationic antiseptic.

In another aspect, the present disclosure is directed to a method for disinfecting mammalian tissue. The method includes applying to the tissue an antimicrobial composition including an aqueous carrier and a surfactant system. The surfactant system includes a PEG compound with an HLB value of greater than about 8 and less than about 14.

In another aspect, the present disclosure is directed to a method for disinfecting mammalian skin, the method including applying to the skin an antimicrobial composition. The antimicrobial composition includes: about 5 wt % to about 95 wt % of an aqueous carrier, based on the total weight of the composition; and about 1 wt % to about 10 wt %, based on the total weight of the composition, of a first surfactant including a polyethylene glycol (PEG) alkyl ester with an HLB value of greater than about 8 and less than about 14.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the drawings indicate like elements.

DETAILED DESCRIPTION

In one aspect, the present disclosure is directed to antimicrobial compositions that can be used to disinfect a wide variety of treatment sites such as, for example, skin, hair, mucosae, wounds, and interior surgical cavities of a patient. The antimicrobial compositions can also be used in personal care compositions, transdermal drug delivery compositions, and the like. The antimicrobial compositions may be applied to the various treatment sites and surfaces in an amount effective to kill microorganisms chosen from bacteria, fungi, viruses, and mixtures and combinations thereof. In various embodiments, the antimicrobial solutions may be in the form of an emulsion, a microemulsion, a soluble solution, a gel, and mixtures and combinations thereof.

The antimicrobial compositions of the present disclosure include one or more polyethylene glycol (PEG) compounds. PEG compounds, also referred to herein as PEGs, together with their derivatives, do not have definite chemical entities, but are compound mixtures having different chain lengths. PEG includes two terminal primary hydroxyl groups that can be used to create mono-, di- and poly-esters, amines, ethers and acetals. PEGs can also create additional compounds and complexes through a reaction in their ether bridges. In the present application the term PEG compound refers to PEG derivatives such as, for example, PEG alkyl ethers (e.g., laureths, ceteths, cetearaths, oleths, and PEG ethers of glyceryl cocoates), PEG alkyl esters (e.g., PEG laurates, dilaurates, stearates, and distearates), PEG castor oils, PEG alkyl amides (e.g., PEG cocamines), PEG propylene glycols, PEG 1,2 diols, and other derivates (e.g., PEG soy sterols and PEG beeswax). Since many PEG types are hydrophilic, they are effective penetration enhancers for use in dermatological preparations. The PEG compounds may be used alone or in combination, or may be used with optional compounds such as any of alkyl esters, alkyl ethers, and alkyl amides, and mixtures and combinations thereof. Any of the alkyl esters, alkyl ethers and alkyl amides can have an alkyl group independently selected to have 8 to 22 carbon atoms. In some embodiments, the alkyl group can include a 1,2 dihydroxy group.

In some embodiments, the PEG compounds and any of the alkyl esters, alkyl ethers, and alkyl amides can be used with optional antimicrobial compounds such as, for example, a cationic antiseptic.

The antimicrobial composition can include any excipient suitable for pharmaceutical use, and can potentially include any PEG compound or combination thereof that is physiologically well tolerated after administration to the skin and/or a mucosa. The PEG compounds have surfactant properties, and the HLB value (Hydrophile-Lipophile Balance) is used in the present application as an empirical expression for the relationship of the hydrophilic and hydrophobic groups of the PEG compound (or any other surfactant in the composition), and in most cases the higher the HLB value, the more water-soluble the surfactant. The selected range of HLB values may vary depending on other additives in the antimicrobial composition.

In the present disclosure, HLB values are calculated using the method of Griffin (Griffin W C; J. Soc. of Cosmetic Chemists, pp. 249-256 (1954)). Thus, as used herein, the "HLB Method" involves a calculation based on the following: HLB=(E+P)/5, where E is the weight percent of oxyethylene content and P is the weight percent of alcohol content (glycerol, sorbitol, etc.). For the compounds herein, glycerol segments with two hydroxyl groups, glycerol segments with one hydroxyl group, and hydroxyl-containing segments of any additional polyhydric molecules were included in the definition of P.

Other methods of calculating the HLB value are available and may be required when determining the HLB value for compounds lacking both E and P groups, as defined above. While the calculated value of HLB may vary depending on the method used, the trends and relative hydrophobicity of materials are expected to be similar.

In various embodiments, which are not intended to be limiting, the PEG compound is chosen from PEG alkyl esters, PEG alkyl ethers, PEG alkyl amides, PEG 1,2 diols, and mixtures and combinations thereof, wherein where the alkyl group on any of the PEG compounds can be independently selected to have 8 to 22 carbon atoms. In some embodiments, the alkyl groups on any of the PEG compounds can include a 1,2 dihydroxy group.

In some embodiments, the PEG compound is a PEG alkyl ester with an alkyl group having 8 to 22 carbon atoms. The PEG alkyl esters, which can also be referred to in the art as PEG fatty acid esters, are the reaction products of a PEG compound (hereafter referred to as a PEG) and a fatty acid. The PEG in the PEG alkyl ester forms a hydrophilic part of the molecule and the C8-C22 alkyl ester component of the PEG alkyl ester forms a lipophilic part of the molecule. By varying the molecular weight of the PEG and the alkyl ester components of the PEG alkyl ester, surfactants covering a wide range of HLB values can be produced. In various embodiments, the PEG alkyl ester compounds in the antimicrobial composition have an HLB value of greater than about 8 and less than about 18, or greater than 8 and less than about 14, or greater than about 10 and less than about 14. In various embodiments, the PEG alkyl ester is a monoester, a diester or a triester, or a mixture or combination thereof. In some embodiments, the PEG alkyl ester is substantially free of triesters, and in some embodiments the PEG alkyl ester is substantially free of both triesters and diesters, and as such consists substantially of monoesters.

In one example embodiment, the antimicrobial composition includes a surfactant system with a first surfactant including one or more first PEG compounds with an HLB value of greater than about 10 and less than about 14. The first surfactant can be chosen from PEG alkyl esters, PEG alkyl ethers, PEG alkyl amides, and mixtures and combinations thereof, wherein the alkyl group on any of the PEG compounds can be independently selected to have 8 to 22 carbon atoms. In some embodiments, the alkyl groups on any of the PEG compounds can include a 1,2 dihydroxy group. The antimicrobial composition further includes a second surfactant with an HLB value of less than about 10, and an optional third surfactant with an HLB value of greater than about 14. The second surfactant and optional third surfactant discussed in more detail below can be independently selected from: (1) one more second PEG compounds, which may be selected from any of the PEG compounds discussed above, and which may be the same or different from the first PEG compounds used as the first surfactant; or (2) alkyl esters, alkyl ethers, and alkyl amides, and mixtures and combinations thereof, wherein the alkyl group in any of the alkyl esters, alkyl ethers, and alkyl amides can be independently selected to have 8 to 22 carbon atoms. In some embodiments, the alkyl groups on any of the alkyl esters, alkyl ethers and alkyl amides can include a 1,2 dihydroxy group.

In some embodiments, the second surfactant includes an alkyl ester with an alkyl group having 8 to 22 carbon atoms, which may be a monoester, diester, triester, or a mixture or combination thereof. In some embodiments, the alkyl ester is chosen from monoester and diesters, and mixtures and combinations thereof. In some embodiments, the alkyl ester is a monoester.

In various embodiments, the PEG compound utilized as one of the surfactants in the antimicrobial composition is a PEG alkyl ester that is a reaction product of a fatty acid component chosen from C8 to C22 fatty acids (fatty acids with 8 to 22 carbon atoms), or C8 to C18 fatty acids, or C8 to C12 fatty acids; and a PEG component with 6 to 60 ethylene oxide units, or 6 to 40 ethylene oxide units, or 6 to 32 ethylene oxide units, or 6 to 10 ethylene oxide units.

In one embodiment, the PEG alkyl ester is a reaction product of an ethoxylated glyceride and a fatty acid. In some embodiments, the fatty acid is a C8 to C22 fatty acid, and a PEG with 6 to 60 ethylene oxide units. In another embodiment, the PEG alkyl ester is a reaction product of a C8 to C18 fatty acid, and a PEG with 6 to 32 ethylene oxide units.

In various example embodiments, the PEG alkyl ester is chosen from PEG 12 glyceryl laurate, PEG 20 glyceryl laurate, PEG 30 glyceryl laurate, PEG 20 glyceryl stearate, PEG 7 cocoate, PEG glyceryl caprate, and mixtures and combinations thereof.

In any of the embodiments above, the PEG alkyl ester can include a mixture of mono, di, and tri esters. In some embodiments, the PEG alkyl ester includes a mixture of monoesters and diesters, and is substantially free of tri esters, or free of tri esters. In some embodiments, the PEG alkyl ester includes monoesters and is substantially free of diesters and triesters, or free of diesters and triesters.

In some example embodiments, the PEG alkyl ester is a reaction product of a PEG and a C8 to C22 fatty acid triester, a reaction product of a PEG and a C8 to C22 fatty acid monoester or diester, or a reaction product of a PEG, a C8 to C22 fatty acid monoester or diester, and a fatty acid mono, di and triester.

In various embodiments, the PEG compounds are present in the composition at about 1 wt % to about 10 wt %, based on the total weight of the composition.

Suitable commercially available PEG alkyl esters include, but are not limited to, those available under the trade designation LABRAFIL from Gattefossé, Lyon, FR, (HLB=9), LABRASOL from Gattefossé (HLB=12), and TEFOSE from Gattefossé (HLB=9-10).

In some embodiments, an optional third surfactant with an HLB value of greater than about 14 and up to about 18 may be included in the antimicrobial composition. In some cases, the high HLB third surfactant can improve the solubility of a second low HLB surfactant in a carrier in the antimicrobial composition. Suitable examples of the high HLB third surfactant include, but are not limited to, PEG alkyl esters, PEG alkyl ethers, PEG alkyl amides listed above, and mixtures and combinations thereof, as well as any of alkyl esters, alkyl ethers, and alkyl amides listed above, and mixtures and combinations thereof. In one embodiment, the third surfactant can include PEG hydrogenated castor oils such as those available from BASF, Florham Park, NJ, under the trade designation KOLLIPHOR (HLB=14-16), and the like, non-ionic or zwitter ionic surfactants like TWEEN, and betaines.

In some non-limiting embodiments, alkyl esters that can optionally be utilized as the second and third surfactants in the antimicrobial composition can include any reaction product of a fatty acid and an alcohol.

Suitable alcohols include, but are not limited to, glycerol, 1,2 propane diol, 1,3-propanediol, diacylgalactosylglycerol, diacyldigalactosylglycerol, erythritol, xylitol, adonitol, arabitol, mannitol, sorbitol, polyglycerol, and mixtures and combinations thereof.

Suitable examples of alkyl esters include, but are not limited to, an ester of glycerol with a fatty acid, an ester of propylene glycol with a fatty acid, and mixtures and combinations thereof.

In various embodiments, which are not intended to be limiting, the alkyl esters have an alkyl group with 8 to 22 carbon atoms, and are derived from a fatty acid chosen from oleic, linoleic, linolenic, caproic, caprylic, capric, lauric, and mixtures and combinations thereof. In some embodiments, the alkyl ester is derived from caprylic acid, capric acid, and mixtures and combinations thereof. In some embodiments, the alkyl esters include monoglycerides, diglycerides and triglycerides of caprylic acid, monoglycerides, diglycerides and triglycerides of capric acid, and mixtures and combinations thereof. In some embodiments, the fatty acid is chosen from glyceryl mono, di, and tri caprylate, glyceryl monocaprylate and dicaprylate, and glyceryl monocaprylate.

In any of the embodiments above, the alkyl ester can include a mixture of mono, di, and tri esters. In some embodiments, the alkyl ester includes a mixture of monoesters and diesters, and is substantially free of tri esters, or free of tri esters. In some embodiments, the alkyl ester includes monoesters and is substantially free of diesters and triesters, or free of diesters and triesters.

Suitable alkyl esters include, but are not limited to, those available under the trade designation CAPMUL from Abitec, Columbus, OH (HLB=6).

In various embodiments, the alkyl esters, alkyl ethers, and alkyl amides are present in the antimicrobial composition at about 1 wt % to about 10 wt %, based on the total weight of the composition.

In some embodiments, the antimicrobial composition includes preservatives such as, for example, benzyl alcohol, phenoxy ethanol, and combinations thereof. In one non-limiting example, the alcohol is present in the composition at about 1 wt % to about 5 wt %, based on the total weight of the composition.

The antimicrobial composition optionally includes at least one antimicrobial compound. Suitable antimicrobial compounds include chlorhexidine salts; octenidine salts, benzalkonium chloride, parachlorometaxylenol (PCMX); triclosan; hexachlorophene; fatty acid monoesters of glycerin and propylene glycol such as glycerol monolaurate, glycerol monocaprylate, glycerol monocaprate, propylene glycol monolaurate, propylene glycol monocaprylate, propylene glycol monocaprate; phenols; surfactants and polymers that include a C12-C22 hydrophobe and a quaternary ammonium group; polyquaternary amines such as polyhexamethylene biguanide; quaternary silanes; hydrogen peroxide; silver and silver salts such as silver chloride, silver oxide and silver sulfadiazine iodine and its complexed forms, which are commonly referred to as iodophors. Iodophors are iodine complexes with polyethylene glycol and its derivatives, N-vinyl caprolactam containing polymers such as polyvinylpyrrolidone, as well as other polymers that tend to hydrogen bond with hydrogen iodide or hydrogen triiodide or complex with salts such as sodium or potassium triiodide. In some embodiments, the iodophor is povidone-iodine, and most preferably povidone-iodine USP, and the like.

In some embodiments the antimicrobial compound is chosen from polymeric biguanides, polymeric (bis) biguanides, and mixtures and combinations thereof. In some embodiments, the antimicrobial compound is chosen from polyhexamethylene biguanide (PHMB), chlorhexidine, octenidine, salts thereof, and mixtures and combinations thereof. In some embodiments, the chlorhexidine is a soluble salt, and the diacetate and digluconate salts have been found to be particularly useful in the antimicrobial composition. In various embodiments, octenidine could be in the form of the dihydrochloride or other suitable salts such as gluconate, citrate, lactate, and the like. In some embodiments, the antimicrobial compound includes chlorhexidine gluconate (CHG), also referred to as chlorhexidine digluconate, or consists of CHG. CHG is a chemical antiseptic that is effective on both gram-positive and gram-negative bacteria. CHG is both bacteriocidal (kills) and bacteriostatic (stops reproductions) of any bacteria on mammalian skin.

In some embodiments, which are not intended to be limiting, the antimicrobial compound is present in the antimicrobial composition at about 0.05 wt % to about 10 wt %, or about 0.1% wt % to about 5 wt %, or about 0.1 to 0.4% or about 1 wt % to about 3 wt %, or about 1.5 wt % to about 2.5 wt %, based on the total weight of the composition (±1%).

The antimicrobial composition can optionally include less than about 10 wt %, or less than about 5 wt %, or less than about 1 wt %, or about 0 wt %, of lower monohydric alcohols, based on the total weight of the composition (±1%). In the present application the term lower monohydric alcohols refers to alcohols with a single hydroxyl group and the formula $C_nH_{2n+1}OH$, wherein n=2 to 5, such as, for example, methanol, ethanol, propanol, isopropyl alcohol, and the like. For example, in some embodiments the antimicrobial composition includes up to about 5 wt %, or up to about 4 wt %, or up to about 3 wt %, of a lower monohydric alcohol such as, for example, isopropanol, which can provide the composition with properties such as enhanced mold resistance.

The reduced amount of C2-C5 monohydric alcohols also provides the antimicrobial composition with good flammability properties when used in a medical or surgical setting, particularly when electrocautery procedures are performed. In some embodiments, for example, the antimicrobial composition has no closed cup flash point at temperatures of 70° F. to 200° F. as measured according to ASTM D-3278-96 e-1.

In various embodiments, the aqueous carrier is present in the antimicrobial composition in an amount of about 5 wt % to about 98 wt %, or about 10 wt % to about 90 wt %, based on the total weight of the composition (±5%). In various embodiments, the aqueous hydrophilic component includes at least about 80 wt % water, or at least about 90% water, based on the total weight of the aqueous hydrophilic component (±5%). In some embodiments, the aqueous carrier consists of water, which in this application means that the aqueous carrier is substantially 100% water, or 100% water, based on the total weight of the aqueous carrier (±1%). In some embodiments, the aqueous carrier can optionally include includes predominantly aqueous solutions such as buffers.

In some embodiments, the aqueous carrier in the antimicrobial composition further optionally includes an alcohol chosen from benzyl alcohol, phenoxy ethanol, isopropyl alcohol, ethanol, and mixtures and combinations thereof. In various embodiments, which are not intended to be limiting, the alcohol is present in the antimicrobial composition at about 1 wt % to about 10 wt %, based on the total weight of the composition.

In some embodiments, the aqueous carrier in the antimicrobial composition further includes a humectant. As used herein the term "humectant" refers to polar compounds or mixtures of compounds that act to retain or absorb moisture. Suitable humectants include, but are not limited to, polyols, such as glycerin, propylene glycol, dipropylene glycol, polypropylene glycol, glycerine ethoxylates, methyl glucose ethoxylates, polyethylene glycol, polyethylene/polypropylene glycols, and sorbitol. In some embodiments, the humectants include liquid polar solvents such as for example, monoalkyl glycols, glycerol alkyl ethers, monoacyl glycerols, and mixtures and mixtures and combinations thereof. Suitable examples of the liquid polar solvents include, but are not limited to, glycerol, propylene glycol, polyethylene glycol, pentylene glycol, and mixtures and combinations thereof.

Diols such as propylene glycol and pentylene glycol are well tolerated by the skin, and have high affinity to skin and hair. In some embodiments, the diols have a small relatively lipophilic molecular region by virtue of which they may also be considered as somewhat amphiphilic, thus enhancing the solubilization of poorly water-soluble ingredients. In some embodiments, the diols can have substantial antimicrobial properties so that they allow for the formulation of aqueous antimicrobial compositions without any further preservatives, or with reduced preservative levels.

In some embodiments, the aqueous carrier can be a mixture of water and a liquid glycol such as, for example, propylene glycol, pentylene glycol and mixtures thereof. For such mixtures, the ratio of water to glycol (or glycols) may be about 1:10 to about 10:1, or about 1:8 to about 8:1, or about 1:5 to about 5:1. Examples of useful aqueous carriers include water and pentylene glycol (2:1), water and propylene glycol (1:2) In various embodiments, the liquid glycol is present in the antimicrobial composition in any amount of about 0 wt % to about 50 wt %, or about 1 wt % to about 30 wt %, or about 5 wt % to about 20 wt % (±1%), based on the total weight of the antimicrobial composition.

Propylene glycol, in addition to playing the role of a humectant in the composition, can help increase the solubility of the low HLB surfactant. Certain formulations containing high levels of HLB can have extreme foaming and would be unacceptable for a bathing product. In some formulations, propylene glycol can substantially reduce foaming.

In some embodiments, the optional addition of low levels of stabilizing ingredients in the aqueous carrier can also be advantageous. Salts such as magnesium sulfate may be useful, but the addition of magnesium sulfate can, in some instances, inactivate any bioactive agents, e.g., antimicrobial agents optionally present in the antimicrobial composition such as chlorhexidine gluconate (CHG) that may optionally be included in the antimicrobial composition. The addition of water-soluble gums such as guar derivatives, xanthan gum, and thickeners such as hydroxy ethyl cellulose, hydroxy propyl cellulose and carboxyl vinyl polymers may be helpful in stabilizing the antimicrobial composition. Suitable oil phase emulsion stabilizers include, but are not limited to, ethylene/acrylic acid copolymers such as those available under the trade designation AC540 from Allied Signal, Morrison, N.J., and N-vinyl pyrrolidone/olefin copolymers such as that available under the trade designation GANEX V-216 from ISP International Specialty Products, Wayne, N.J.

In one example embodiment, which is not intended to be limiting, the antimicrobial composition includes about 5 wt % to about 95 wt % of an aqueous carrier, based on the total weight of the composition; and about 1 wt % to about 10 wt %, based on the total weight of the composition, of a first surfactant including a PEG compound such as, for example, a PEG alkyl ester, with an HLB value of greater than about 8 and less than about 14.

In another example embodiment, the composition may optionally include about 1 wt % to about 10 wt %, based on the total weight of the composition, of a cationic antiseptic chosen from octenidine, biguanides, bisbiguanides, polymeric biguanides, polymeric (bis)biguanides, benzalkonium chloride, alexidine dihydrochloride, cetyl pyridinium chloride, salts thereof, and mixtures and combinations thereof.

In another example embodiment, which is not intended to be limiting, the antimicrobial composition includes about 5 wt % to about 95 wt % of an aqueous carrier, based on the total weight of the composition; about 1 wt % to about 10 wt %, based on the total weight of the composition, of a first surfactant including a first PEG compound such as, for example, a PEG alkyl ester, with an HLB value of greater than about 10 and less than about 14; and about 1 wt % to about 10 wt %, based on the total weight of the composition, of a second surfactant, different from the first surfactant, wherein the second surfactant has an HLB value of less than about 10. The second surfactant is chosen from a second PEG compound different from the first PEG compound, an alkyl ester, an alkyl ether, an alkyl amide, and mixtures and combinations thereof, wherein the alkyl esters, ethers and amides have an alkyl group independently selected to have 8 to 22 carbon atoms. In some embodiments, the alkyl group in any of the alkyl esters, alkyl ethers and alkyl amides can include a 1,2 dihydroxy group.

In another example embodiment, the composition may optionally include about 1 wt % to about 10 wt %, based on the total weight of the composition, of a cationic antiseptic chosen from octenidine, biguanides, bisbiguanides, polymeric biguanides, polymeric (bis) biguanides, benzalkonium chloride, alexidine dihydrochloride, cetyl pyridinium chloride, salts thereof and mixtures and combinations thereof.

In another example embodiment, any of the example antimicrobial compositions above can include an optional third surfactant with an HLB value of greater than about 14 and up to about 18 such as, for example, PEG compounds, alkyl esters alkyl ethers, and alkyl amides listed above, and mixtures and combinations thereof.

In some embodiments, the antimicrobial composition can optionally include emollient oils such as, for example, silicone fluids, saturated fatty esters and diesters such as diisopropyl adipate, dicapryl adipate, diisopropyl sebacate, dioctyl sebacate, dioctyl ether, glyceryl tricaprylate/caprate, diethyleneglycol dicaprylate/caprate, propylene glycol dipelargonate, polyalkoxylated alcohols such as 15 mole propoxylate of stearyl alcohol, paraffin oils and waxes, animal and vegetable oils including mink oil, coconut oil and derivatives thereof, palm oil, corn oil, cocoa butter, petrolatum, coconut oil, sesame oil, and the like, lanolin derivatives, fatty alcohols such as isostearyl alcohol, isocetyl alcohol, cetyl/stearyl alcohol, and straight chain alcohols from C6-C18 and certain petroleum distillates which are toxicologically safe such as C8-C22 isoparaffin hydrocarbon solvents, e.g., isooctane and isododecane, mixtures of mono, di and tri glycerides of long chain fatty acids, mixtures of propylene glycol mono, di and tri esters of fatty acids. In some embodiments, the same excipients can act as the surfactant component of the composition, depending on how they are formulated (i.e. the remaining excipients).

In some embodiments, the addition of a silicone oil such as dimethicone to the lipophilic component to prepare the microemulsion can also be advantageous in improving the ability of the antimicrobial compositions to act as a barrier to urine, feces, or other indigenous and exogenous materials when used as moisturizing compositions (e.g., moisturizing skin treatments). In some embodiments, the dimethicone may be present at about 1 wt % to about 5 wt %, based on the total weight of the composition (±1%). In some embodiments, aloe may be used to help improve the solubility of the dimethicone in the composition to provide further moisturization.

In some embodiments, the antimicrobial composition may optionally include auxiliary emulsifiers conventionally used in cosmetic formulations to ensure stability and extend shelf life of any of the compositions of the present invention. Suitable auxiliary emulsifiers include, but are not limited to, C12-C18 alkyl carboxylic acids such as stearic acid, polypropylene glycol (PPG) (15) stearyl ether (commercially available under the trade designation ARLAMOL E from Uniqema, Wilmington, Del.), and 20-mole ethoxylate of cetyl/stearyl alcohol, polyetherpolyester polymer, such as polyethylene glycol (PEG) (30) polyhydroxy-stearate, MW of approximately 5000 (commercially available under the trade designation ARLACEL P135 from ICI, Wilmington, Del.). In various embodiments, the auxiliary emulsifier is preferably present in an amount of about 1 wt % to about 20 wt %, or about 5 wt % to about 10 wt %, based on the total weight of the antimicrobial composition.

In various embodiments, the antimicrobial compositions may include further components as required. For example, the antimicrobial compositions may optionally include a further active ingredient, e.g. a corticosteroid, an antibiotic, an antimycotic, and/or an antiviral agent.

The antimicrobial composition may further include up to about 5 wt %, or up to about 4 wt %, or up to about 3 wt %, based on the total weight of the composition, of other optional ingredients including, for example, agents for adjusting the pH (e.g. acids, buffer salts, bases), antioxidants (e.g. ascorbic acid, vitamin E and its derivatives, BHT, BHA, disodium EDTA, etc.), preservatives (e.g. cationic surfactants such as benzalkonium chloride; benzyl alcohol, sorbic acid etc.), permeation enhancers (DMSO, diethylene glycol monoethyl ether (DEGEE) available under the trade designation TRANSCUTOL from Gattefossé, Paramus, NJ, menthol, oleic acid, n-alkanols, dimethyl isosorbides, 1-alkyl-2-pyrrolidones, N,N-dimethlyalkanamides, and 1,2-alkanediols, etc.), and the like.

Other materials conventionally used in cosmetic compositions such as waxes, film-forming polymers, propellants, buffers, organic or inorganic suspending or thickening agents, plasticizers, and herbal extracts can also be included in minor amounts in the antimicrobial compositions, preferably in amounts that do not adversely affect the substantivity of the compositions. These materials can be added to the aqueous carrier or surfactant system (depending on solubility), or added after the aqueous carrier and the surfactant system have been prepared and cooled. The latter is preferred when materials with heat sensitivity are used.

The antimicrobial composition may be in the form of a liquid or a gel, i.e. in liquid or semisolid form.

In some embodiments, the antimicrobial composition is optically isotropic, which is this application refers to a material having physical properties that are substantially the same when measured in different directions. In some embodiments, the antimicrobial compositions are translucent to visible light (about 400 nm to about 750 nm) at room temperature, which means that the microemulsions pass visible light but do not allow viewing of detailed images therethrough. In other embodiments, the antimicrobial compositions appear substantially transparent or clear to visible light at room temperature. In this application the term substantially transparent refers to materials that pass visible light in the wavelength region sensitive to the human eye, while rejecting light in other regions of the electromagnetic spectrum. In some embodiments, the reflective edge of the antimicrobial composition should be above about 750 nm, just out of the sensitivity of the human eye.

The antimicrobial compositions are stable, which in the present application means that the antimicrobial composition remains optically isotropic and in its as-formulated translucent or substantially transparent form for a period of at least about 6 months at room temperature (±1 month). In some embodiments, the antimicrobial composition is stable for a period of about 6 months to about 2 years at room temperature (±1 month). In this application, stable means that the antimicrobial composition is able to kill bacteria in the time kill test after aging. In some cases, even if there is phase separation, the phase-separated product has the ability to kill bacteria in the time kill test when mixed before testing. In some embodiments, the antimicrobial compositions may be applied directly on mammalian skin, mucosal tissue, hair, mucosae, wounds, surgical cavities, and the like to disinfect the site. In various embodiments, the antimicrobial compositions may be applied using a wide variety of applicators including, but not limited to, foam applicators, sponges, a woven or nonwoven cloth, a woven or nonwoven mitt, and the like. In some embodiments, the foam applicator includes a compressed foam. In some embodiments, the antimicrobial composition may be supplied as a layer on a surface of a surgical incise drape or a surgical tape, or may be impregnated into the surface of the surgical incise drape or a surgical tape.

In various embodiments, the antimicrobial composition is sufficiently effective against microorganisms on the surface of mammalian skin, mucosae, hair, wounds, surgical cavities, and the like, and provides at least a 0.5-log microbial reduction, at least a 1.5-log microbial reduction, at least a 2-log reduction, or at least a 3 log reduction, following 10 minutes and 24 hours contact time as measured according to ASTM E18474.

In some embodiments, the antimicrobial composition is also highly persistent on the surface of mammalian skin, mucosae, bone, hair, wounds, surgical cavities, and the like. In this application persistence refers to microbial counts not returning to baseline at a set time, for example 24 hour persistence would be that for 24 hours, the microbial counts have not returned to pre-treatment levels. Efficacy for 24 hours refers to having low bacterial bioburden for a period of 24 hours. A formulation that has high efficacy at 24 hours means that it has very few bacteria left on skin after a period of 24 hours.

In some embodiments, the antimicrobial composition prevents microbial counts from returning to baseline for at least 24 hours, at least 48 hours, or at least 72 hours. In some embodiments, the antimicrobial composition has excellent efficacy for a period of at least 24 hours, at least 48 hours, or at least 72 hours. In some embodiments, the antimicrobial composition has both persistence and high efficacy for a period of at least 24 hours, at least 48 hours, or at least 72 hours.

In various embodiments in which an antimicrobial compound is present in the antimicrobial composition, the antimicrobial composition reduces viable bacterial counts by at least 5 log orders within 10 seconds, while the vehicle (composition without the antimicrobial compound) reduces viable bacterial counts by less than 0.5 log orders within 10 seconds in solution.

Figure 1:
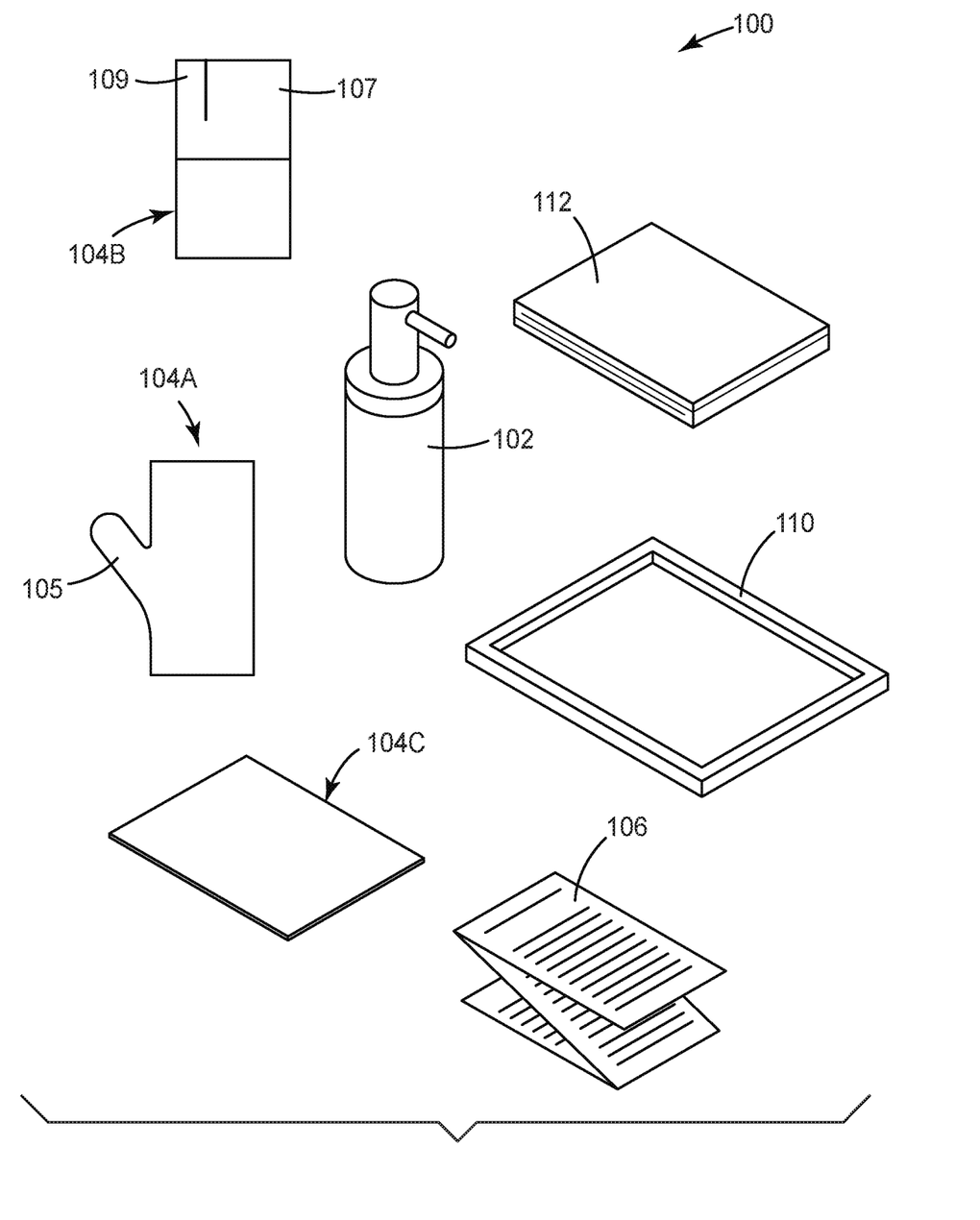
The FIGURE is a schematic diagram of components of a kit including applicators that can be used to apply the antimicrobial compositions of the present disclosure to the skin of a patient.

Referring to the FIGURE, in some example embodiments, the antimicrobial composition may be supplied in the form of a kit 100 including a container 102 of the antimicrobial composition and an applicator 104 that can be used to apply the antimicrobial composition to the skin. In some example embodiments, the container 102 may be a squeezable bottle or a collapsible tube, along with instructions 106 for proper application to a treatment site or to the included applicator 104. In one example, the applicator is a mitt such as shown in the FIGURE as 104A, 104B. In another embodiment, the applicator may be a substantially flat cloth, wipe or sponge 104C. In another embodiment, the antimicrobial composition may be impregnated in a surface of the applicators 104A,104B,104C.

In some embodiments, the kit may be supplied in sterile form in a tray 110, and may optionally include the application instructions 106 along with a surgical incise drape 112. In some embodiments, the tray 110 and drape 112 may be packaged for a selected medical or surgical procedure.

The antimicrobial composition can be easily manufactured and scaled up into industrial scale production. The antimicrobial composition can be formed as the ingredients are combined and mixed together, even in the absence of high shear conditions or pressure homogenization. Therefore, the antimicrobial composition may be prepared using any standard mixing equipment which is suitable for the preparation of liquid pharmaceutical formulations at the appropriate scale. Optionally, ultrasound treatment of the combined ingredients may be used to accelerate formation.

In some applications, the composition could include an FDA acceptable dye and in other cases, the dye could be separated from the composition within the applicator.

A variety of ingredients or combination of ingredients and active agents can be utilized to obtain a cosmetic formulation optimized for a particular utility or market segment and a reference source that lists standard cosmetic ingredients is the International Cosmetic Ingredient Dictionary and Handbook, published by The Cosmetic, Toiletry, and Fragrance Association, John A. Wenninger and G. N. McEwen, Jr., Editors, 7th Edition, 1997.

In one example embodiment, the antimicrobial composition may be made by initially preparing a precursor composition including a surfactant system, and an aqueous hydrophilic component. Addition to the precursor composition of an optional antimicrobial compound chosen from polymeric biguanides, polymeric (bis) biguanides, and mixtures and combinations thereof forms a stable microemulsion at room temperature with a disperse phase having droplets with a particle size of about 5 nm to about 400 nm.

Embodiments of the invention will now be illustrated with reference to the following non-limiting examples.

EXAMPLES

Example 1: Test Method 1: In Vitro Time Kill Test Method for Antiseptic Solution This method is based on ASTM E2315-16 Standard Test Method of Assessment of Antimicrobial Activity Using a Time Kill Procedure. A suspension of bacteria was added to a volume of the test formulations and controls, and at desired time points a determined volume was pipetted into a neutralizer to stop antimicrobial activity. The neutralizer tubes were vortexed, serially diluted and plated for enumeration of surviving bacteria. Preliminary time kill experiments with 2% CHG indicated that timepoints of 10 seconds and 2 minutes provide useful screening information on rapid bacterial kill for active formulations (10 seconds), and the level of antimicrobial activity in vehicles in comparison (up to 2 minutes)

Materials

Dey-Engley Neutralizing Broth (DE), prepared from Difco powder

Phosphate buffered water (PBW; lab prepared)

Tryptic Soy Agar (TSA) for enumeration

Bacteria

*Staphylococcus aureus* ATCC 25923, suspended to approximately 1E8 logs/mL PBW using a McFarland 0.5 turbidity standard Method 2 mL of Test formulations and controls was placed into sterile tubes. One hundred microliters of the bacteria suspended to approximately 1E8 logs/ml was pipetted directly into each formulation. Separate tubes were set up for the 10 second and 2 minute time points (ambient temperature). At the end of each time interval, 200 µL was immediately transferred to 25 mL DE broth and vortexed. Serial dilutions were prepared from each neutralizer tube, and each dilution was pour plated with TSA for enumeration of the surviving bacteria. Plates were incubated at 35° C. for 24-48 hours.

The inoculum concentration (Numbers Control) was determined by adding 100 uL bacteria to 2 mL PBW for 2 minutes, and similarly transferred to 25 mL DE neutralizer tubes.

Analysis

Plate counts were recorded and the recovery per sample was determined. Recoveries were transformed to $Log_{10}$CFU/sample for all test samples and Numbers Controls. The mean of the $Log_{10}$ Numbers Controls was calculated. Log Reduction from each test sample was determined by subtracting the Log Recoveries of the Test samples from the mean Log of the Numbers Controls.

Example 2: Test Method 2: Endogenous Biopsy Punch Model, 10 Min and 24 h

Tissue Preparation

Abdominal skin from two Yorkshire pigs was transported to the laboratory on ice. An adequate amount of sample was excised from each pig for the required number of explants and then rinsed under cold running water by holding it under the faucet and rubbing gently to remove blood, clots, dirt, etc. Rinsed skin was blotted dry with paper towels and shaved with an Oster Golden A5 electric shaver, size 10 blade. Skin was rinsed again to remove shaved bristles and remaining debris and blotted dry with paper towels.

Explant Creation

Cleaned, shaved skin section was transferred to a wax dissection tray, skin side up, and forceps were used to stabilize a 5-mm biopsy punch and explants were made by pressing down on the punch with a gentle twisting motion. Explants were transferred to a petri dish with RPMI and washed 3× in ~10 ml of RPMI. After washing, explants (n=3 per treatment group well) were transferred to 6-well plates, with each well containing a 0.4 um transwell insert and 2.0 ml of RPMI. Plates were incubated at 37±2° C., 7% $CO_2$ for 2±0.25 h.

Treatment

Each explant was either untreated or treated with 50 ul of formulation. Plates were then incubated at 37±2° C., 7% $CO_2$ for 24 hours±4 hours.

Sampling

At the end of the incubation period, explants were transferred to 14 mL tube containing 5±0.1 mL of SST neutralizer. Tubes were then vortexed for 30±5 s, sonicated for 2±0.5 min sonicate, and vortexed for 30±5 s. Samples were diluted with PBS if deemed necessary and plated onto TSA with 5% sheep's blood Plates were incubated overnight at 37±2° C., ambient $CO_2$.

Enumeration and Analysis

After the 48 h incubation, colonies were counted on a colony counter and log CFUs/ml were calculated. Significant differences compared to growth control (no treatment group) or Sage were analyzed by one-way ANOVA followed by Dunnett Post test ($p<0.05$).

Example 3: Table Showing Details of Chemicals Purchased

| No. | Chemical name | Trade name | Company | Location |
|---|---|---|---|---|
| 1 | Glyceryl Monocaprylate | Capmul 808 g | Abitec | Columbus, OH |
| 2 | Glyceryl Monocaprylate | Capmul 708 g | Abitec | Columbus, OH |
| 3 | PEG-12 glyceryl laurate | — | Global 7 | Cambridge, OH |
| 4 | Oleoyl polyoxyl-6 glycerides | Labrafil M 1944 | Gattefosse | Lyon, France |
| 5 | Caprylocaproyl Polyoxyl-8 glycerides | Labrasol | Gattefosse | Lyon, France |
| 6 | PEG-40 hydrogenated castor oil | Kolliphor RH40 | Sigma Aldrich | St. Louis, MO |
| 7 | Propylene glycol | — | Sigma Aldrich | St. Louis, MO |
| 8 | Phenoxyethanol | — | Sigma Aldrich | St. Louis, MO |
| 9 | Isopropanol | — | Sigma Aldrich | St. Louis, MO |
| 10 | Chlorhexidine gluconate | — | Medichem | Germany |
| 12 | PEG-12 laurate | — | Parchem | New Rochelle, NY |
| 13 | PEG-6 stearate/ethylene glycol palmitostearate/PEG-32 stearate | Tefose 63 | Gattefosse | Lyon, France |
| 14 | PEG-6 stearate/PEG-32 stearate | Tefose 1500 | Gattefosse | Lyon, France |
| 15 | PEG distearate | — | | |
| 16 | ethoxylated lanolin | Solulan 75 | Lubrizol | Calvert City, KY |
| 17 | polyglycerol oleate | — | Abitec | Columbus, OH |

Example 4: CAPMUL/LABRAFIL/LABROSOL Formulas

If the reagent was solid like CAPMUL and KOLLIPHOR RH 40, they would be melted by heating to 40° C. for a brief while.

CAPMUL, LABROFIL, LABROSOL, and KOLLIPHOR were added to the mixing vessel, then stirred vigorously. Propylene glycol, phenoxyethanol, isopropanol, chlorhexidine gluconate was added to the same vessel and again stirred vigorously. Finally, water was added and stirred a third time.

| | Formulation no. | | | | | | | | | |
|---|---|---|---|---|---|---|---|---|---|---|
| | 1 | 2 | 3 | 4 | 5 | 6 | 7 | 8 | 9 | 10 |
| Capmul | 0.5 | 0.5 | 0.5 | 0.5 | — | — | — | — | — | — |
| Labrofil | 1 | 1 | — | — | 1 | 1 | — | — | 1 | 1 |

-continued

|  | Formulation no. | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Labrasol | 2 | 2 | — | — | — | — | 0.5 | 0.5 | 0.5 | 0.5 |
| Kolliphor | 3 | 3 | — | — | 3 | 3 | — | — | 3 | 3 |
| Propylene glycol | 10 | 10 | 10 | 10 | 10 | 10 | 10 | 10 | 10 | 10 |
| Phenoxyethanol | 1 | 1 | 1 | 1 | 1 | 1 | 1 | 1 | 1 | 1 |
| Isopropanol | 4 | 4 | 4 | 4 | 4 | 4 | 4 | 4 | 4 | 4 |
| Chlorhexidine gluconate | 2.13 | — | 2.13 | — | 2.13 | — | 2.13 | — | 2.13 | — |
| 10 second time-kill (test method 1) | 5.31 | 0.02 | 5.53 | 3.44 | 2.62 | 0.13 | 5.83 | 1.51 | 1.93 | 0.22 |
| 2-minute time-kill (test method 1) | 5.31 | 1.51 | 5.83 | 5.83 | 5.83 | −0.01 | 5.83 | 5.53 | 5.4 | 0.15 |
| Appearance | cloudy | cloudy | clear | clear | cloudy | cloudy | clear | clear | cloudy | cloudy |
| Average log reduction at 24 hours (test method 2) | 4.93 | 2.23 | 7.06 | 0.65 | 4.85 | 1.14 | — | — | — | — |
| SD | 0.84 | 0.61 | 0.48 | 0.33 | 0.72 | 0.41 | — | — | — | — |

For test method 2, baseline was 8.49 log 10CFU+/−0.278.

Appearance of the formulation was assessed typically an hour after preparation. The log reduction was assessed by two test methods −1 and 2, and the log reduction and standard deviation was reported.

Example 5: PEG Glyceryl Laurate/CAPMUL Formulas

PEG-12 glyceryl laurate, CAPMUL, propylene glycol, phenoxyethanol, isopropanol, chlorhexidine gluconate was added to the vessel in order. Finally, water was added and stirred to make a clear solution.

|  | Formulation no. | | | | | | | | | |
| --- | --- | --- | --- | --- | --- | --- | --- | --- | --- | --- |
|  | 1 | 2 | 3 | 4 | 5 | 6 | 7 | 8 | sage | saline |
| PEG-12 glyceryl laurate | 2 | 2 | 2 | 2 | 2 | 2 | 2 | 2 |  |  |
| Capmul | 1 | 1 | — | — | 0.5 | 0.5 |  |  |  |  |
| Propylene glycol monolaurate |  |  |  |  |  |  | 1 | 1 |  |  |
| Propylene glycol | 10 | 10 | 10 | 10 | 10 | 10 | 10 | 10 |  |  |
| Phenoxyethanol | 1 | 1 | 1 | 1 | 1 | 1 | 1 | 1 |  |  |
| Isopropanol | 4 | 4 | 4 | 4 | 4 | 4 | 4 | 4 |  |  |
| Chlorhexidine gluconate | 2.13 | — | 2.13 |  | 2.13 | — | 2.13 | — |  |  |
| 10 second time-kill | 4.37 | 1.15 | 3.64 | 0.21 | 5.11 | 0.15 | 3.85 | 0.22 | 0.51 | — |
| 2-minute time-kill | 5.67 | 5.1 | 5.67 | 1.49 | 5.11 | 1.89 | 5 | 1.76 | 3.21 | −0.19 |
| Appearance | clear | clear | clear | clear | clear | clear |  |  |  |  |
| Log reduction 24 hr | 5.56 | — |  | — |  |  |  | 1.87 |  |  |

Baseline was 8.87 log 10CFU+/−0.545

Sage solution was squeezed out of the 2% CHG cloth and used for the test methods 1 and 2.

Example 6: Formulas with Other Excipients

Tefose 63 was heated until liquid. All other ingredients were added except water. The melted Tefose 63 was added, then immediately vortexed for approximately 30 seconds. After vortexing, water was added and vortexed an additional 30 seconds. If not completely dissolved, the solution was heated until any remaining solid is dissolved.

|  | Formulation no. | | | | | | | | | | | |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| PEG-12 laurate | 2 | 2 | — | — | — | — | — | — | — | — | — | — |
| Tefose 63 | — | — | 1 | 1 | — | — | — | — | — | — | — | — |
| Tefose 1500 | — | — | — | — | 1 | 1 | — | — | — | — | — | — |
| Solulan 75 | — | — | — | — | — | — | 1 | 1 | — | — | — | — |
| PEG distearate | — | — | — | — | — | — | — | — | 1 | 1 | — | — |
| PG oleate | — | — | — | — | — | — | — | — | — | — | 1 | 1 |
| Propylene glycol | 10 | 10 | 10 | 10 | 10 | 10 | 10 | 10 | 10 | 10 | 10 | 10 |
| Phenoxyethanol | 1 | 1 | 1 | 1 | 1 | 1 | 1 | 1 | 1 | 1 | 1 | 1 |
| Isopropanol | 4 | 4 | 4 | 4 | 4 | 4 | 4 | 4 | 4 | 4 | 4 | 4 |
| Chlorhexidine Gluconate | 10.65 | — | 10.65 | — | 10.65 | — | 10.65 | — | 10.65 | — | 10.65 | — |
| 10 Second time-kill | 1.32 | −0.06 | 5.45 | −0.14 | 5.45 | −0.04 | 4.97 | −0.06 | 2.65 | 0.01 | 5.45 | 0.01 |
| 2-minute time-kill | 5.45 | 0.9 | 5.5 | 0.05 | 5.45 | 0.12 | 5.45 | 0.09 | 5.45 | 0.08 | 5.45 | 0.04 |
| Reduction from G.C. Average | — | — | 3.39 | 0.89 | — | — | 3.46 | 0.89 | — | — | 2.27 | 1.07 |
| S.D. | — | — | 0.37 | 0.19 | — | — | 0.34 | 0.193 | — | — | 0.37 | 0.25 |

|  | Growth Control |
| --- | --- |
| Average | 8.575 |
| SD | 0.083 |

|  | Weight percent | | | | | | | |
| --- | --- | --- | --- | --- | --- | --- | --- | --- |
|  | 1 | 2 | 3 | 4 | 5 | 6 | 7 | 8 |
| PEG-12 glyceryl laurate | 2 | 2 | 2 | 2 | — | — | — | — |
| Labrafil | — | — | — | — | 0.5 | 0.5 | 0.5 | 0.5 |
| Labrasol | — | — | — | — | 0.5 | 0.5 | 0.5 | 0.5 |
| kolliphor rh40 | — | — | — | — | 1.5 | 1.5 | 1.5 | 1.5 |
| Capmul | 1 | 1 | — | — | — | — | 0.5 | 0.5 |
| propylene glycol | 10 | 10 | 10 | 10 | 10 | 10 | 10 | 10 |
| phenoxyethanol | 1 | 1 | 1 | 1 | 1 | 1 | 1 | 1 |
| isopropanol | 4 | 4 | 4 | 4 | 4 | 4 | 4 | 4 |
| chlorhexidine gluconate | 2.13 | — | 2.13 | — | 2.13 | — | 2.13 | — |
| Time kill 10 sec | 4.37 | 1.15 | 3.64 | 0.21 | 4.79 | 0.12 | 5.27 | 0.29 |
| Time kill 2 min | 5.67 | 5.10 | 5.67 | 1.49 | 5.67 | 2.03 | 5.67 | 2.55 |

Example 7: Octenidine Formulations

Octenidine formulations were prepared in a similar way as described above. In some cases, the formulation was warmed to 40° C. for a brief while to create a homogenous solution and to enable solubility of octenidine.

|  | 1 | 2 | 5 | 6 | 7 | 8 | 9 | 10 |
| --- | --- | --- | --- | --- | --- | --- | --- | --- |
| Octenedine | 0.4 | — | 0.4 | — | 0.4 | — | 0.4 | — |
| PEG-12 glyceryl laurate | — | — | — | — | 2 | 2 | 2 | 2 |
| Capmul | — | — | — | — | — | — | — | — |
| Pgml | — | — | 1 | 1 | 1 | 1 | — | — |
| Propylene glycol | 10 | 10 | 10 | 10 | 10 | 10 | 10 | 10 |
| Phenoxyethanol | 1 | 1 | 1 | 1 | 1 | 1 | 1 | 1 |
| Isopropanol | 4 | 4 | 4 | 4 | 4 | 4 | 4 | 4 |
| 10 second time-kill | 5.45 | 0.44 | 5.45 | 1.26 | 5.45 | 0.33 | 5.45 | −0.07 |
| 1-minute time-kill | 5.45 | 1.14 | 5.45 | 1.95 | 5.45 | 1.27 | 5.45 | 1.29 |

|  | Growth Control |
| --- | --- |
| Average | 8.4463382 |
| SD | 0.3286545 |

| 032519- | 1 | 2 | 3 | 4 | 5 | 6 | 7 | 8 |
| --- | --- | --- | --- | --- | --- | --- | --- | --- |
| PEG-12 glyceryl laurate | 2 | 2 | — | — | — | — | 2 | 2 |
| labrasol | — | — | 2 | — | | | | |

-continued

| | | | | | | | | |
|---|---|---|---|---|---|---|---|---|
| capmul | 0.5 | 0.5 | 8 | — | | | 0.5 | 0.5 |
| octenedine | 0.4 | — | — | — | 0.4 | 0.4 | 0.1 | — |
| propylene glycol | 10 | 10 | 15 | 15 | 10 | | 10 | 10 |
| phenoxyethanol | 1 | 1 | 1 | 1 | 1 | | 1 | 1 |
| isopropanol | 4 | 4 | 7.5 | 7.5 | 4 | | 4 | 4 |
| tween 20 | — | — | 5 | 5 | | | | |
| Peg 12 chlorhexidine gluconate | — | — | — | — | | | | |
| Stable | Yes | Yes | Yes | Yes | | | | |
| Log reduction after 24 hours | 2.04 | 0.12 | 7.04 | 0.75 | | | | |
| Average standard deviation | 0.70 | 0.262 | 0.47 | 0.20 | | | | |
| Time kill 10 sec | 5.61 | 0.55 | — | — | 5.61 | 5.61 | 5.61 | 0.44 |
| Time kill 2 min | 5.61 | 3.77 | — | — | 5.61 | 5.61 | 5.61 | 3.10 |

| | Growth Control |
|---|---|
| Average | 7.70 |
| SD | 0.16 |

Various embodiments of the invention have been described. These and other embodiments are within the scope of the following claims.

The invention claimed is:

1. An antimicrobial composition, comprising:
   an aqueous carrier present in an amount of about 5 wt % to about 95 wt % based on the total weight of the composition;
   a cationic antiseptic present in an amount of about 1 wt % to about 10 wt % based on the total weight of the composition, the cationic antiseptic selected from octenidine, chlorhexidine, polyhexamethylene biguanide, benzalkonium chloride, alexidine dihydrochloride, cetyl pyridinium chloride, salts thereof, and a combination thereof; and
   a surfactant system comprising:
      a first surfactant present in an amount of about 1 wt % to about 10 wt % based on the total weight of the composition,
         the first surfactant selected from PEG alkyl esters, PEG alkyl ethers, PEG alkyl amides, and a combination thereof, wherein each alkyl group has 8 to 22 carbon atoms,
         the first surfactant characterized by an HLB value of greater than about 10 and less than about 14, and
      a second surfactant present in an amount of about 1 wt % to about 10 wt % based on the total weight of the composition,
         the second surfactant comprising a 1,2-dihydroxy group and selected from an alkyl ester, an alkyl ether an alkyl amide, and a combination thereof, wherein each alkyl group has 8 to 22 carbon atoms
         the second surfactant characterized by an HLB value less than about 10, wherein the first surfactant and the second surfactant are different.

2. The antimicrobial composition of claim 1, further comprising a third surfactant characterized by HLB value of greater than about 14 and less than about 18.

3. The antimicrobial composition of claim 2, wherein the third surfactant is a PEG compound chosen from PEG alkyl esters, PEG alkyl ethers, PEG alkyl amides, and mixtures and combinations thereof, the PEG compounds having an alkyl group independently selected to have 8 to 22 carbon atoms.

4. The antimicrobial composition of claim 1, wherein the first surfactant comprises 6 to 60 ethylene oxide units.

5. The antimicrobial composition of claim 1, wherein the first surfactant is selected from PEG 12 glyceryl laurate, PEG 20 glyceryl laurate, PEG 30 glyceryl laurate, PEG 20 glyceryl stearate, PEG 7 cocoate, PEG glyceryl caprate, polyglycerol oleate and a combination thereof.

6. The antimicrobial composition of claim 1, wherein the composition further comprises an alcohol chosen from benzyl alcohol, phenoxy ethanol, isopropyl alcohol, ethanol, and mixtures and combinations thereof.

7. The antimicrobial composition of claim 6, wherein the alcohol is present in the composition at about 1 wt % to about 10 wt %, based on the total weight of the composition.

8. The antimicrobial composition of claim 1, wherein the aqueous carrier comprises at least about 80 wt % water, based on the total weight of the aqueous carrier.

9. The antimicrobial composition of claim 1, wherein the aqueous carrier comprises glycerol, propylene glycol, polyethylene glycol, pentylene glycol, and mixtures and combinations thereof.

10. The antimicrobial composition of claim 1, wherein the second surfactant is a monoglyceride, derived from a fatty acid chosen from oleic, linoleic, linolenic, caproic, caprylic, capric, lauric, and mixtures and combinations thereof.

11. The antimicrobial composition of claim 1, wherein the cationic antiseptic is chosen from octenidine hydrochloride, polyhexamethylene biguanide, chlorhexidine gluconate, and a combination thereof.

12. The antimicrobial composition of claim 1, wherein the cationic antiseptic is chlorhexidine gluconate.

13. A method of disinfecting a treatment site chosen from skin, hair, mucosae, wounds, and body cavities, the method comprising
   applying to the treatment site an antimicrobial composition of claim 1.

14. The method of claim 13, wherein the composition reduces microorganisms at the treatment site by at least 2 log orders after 10 seconds.

15. The method of claim 13, wherein the composition reduces microorganisms at the treatment site by at least 5 log orders after 10 seconds.

16. The method of claim 13, wherein the composition prevents regrowth of microorganisms at the treatment site for 24 hours.

17. A kit, comprising:
an antimicrobial composition of claim 1; and
an applicator for applying the antimicrobial composition to the skin of a patient.

\* \* \* \* \*